United States Patent [19]

Greene et al.

[11] 4,158,053

[45] Jun. 12, 1979

[54] AQUEOUS EMULSION POLYMER NAIL COATING FORMULATIONS

[75] Inventors: James A. Greene, Carmel; Robert S. Nevin, Indianapolis, both of Ind.; Moustafa M. Sharabash, Egypt

[73] Assignee: Eli Lilly and Company, Indianapolis, Ind.

[21] Appl. No.: 822,040

[22] Filed: Aug. 5, 1977

[51] Int. Cl.$^2$ ............................................. A61K 7/04
[52] U.S. Cl. ........................................ 424/61; 424/78; 424/81
[58] Field of Search ............................. 424/61, 81, 78

[56] References Cited

U.S. PATENT DOCUMENTS

| | | | |
|---|---|---|---|
| 2,887,116 | 5/1959 | Wooding | 132/73 |
| 2,996,432 | 8/1961 | Modderno | 424/47 |
| 3,639,572 | 2/1972 | Heinrich et al. | 424/63 |
| 3,697,644 | 10/1972 | Laiderman | 424/70 |
| 3,927,203 | 12/1975 | Seymour et al. | 424/61 |

FOREIGN PATENT DOCUMENTS

| | | |
|---|---|---|
| 50-28502 | 9/1975 | Japan. |
| 1032367 | 6/1966 | United Kingdom. |
| 1074201 | 6/1967 | United Kingdom. |

*Primary Examiner*—V. D. Turner
*Attorney, Agent, or Firm*—Karen L. Searle; Arthur R. Whale

[57] ABSTRACT

Novel nail coating formulations containing aqueous emulsion polymers which have a $T_g$ range from about $-10°$ C. to 50° C., a solids content from about 30 to 55 percent, and a moisture vapor transmission of the film from about 0.1 to 1.6 mg./cm.$^2$/hr. have improved properties, such as, reduced occlusion, faster drying time, non-yellowing of the nail, and non-flammable solvent.

24 Claims, No Drawings

AQUEOUS EMULSION POLYMER NAIL COATING FORMULATIONS

BACKGROUND OF THE INVENTION

Many types of cosmetic film forming compositions, including nail coating formulations, have been used in the past and are currently on the market.

Most nail coatings now available are lacquers and consist of nitrocellulose, aryl sulfonamide formaldehyde resin, plasticizer and solvent mixture together with a small proportion of color and pigment. These nail lacquers have the disadvantages of discoloration of the nail (keratin), of having a flammable solvent present, of having a rather high occlusion of the nail, and of requiring a rather long drying time.

The present nail coating formulation contains as the film-forming component an aqueous emulsion polymer which is prepared by polymerization of monomers in water. The emulsion has a solids content from about 30 to 55 percent and films made from the emulsion have a moisture vapor transmission from about 0.1 to 1.6 mg./cm.$^2$/hr. The polymer has a $T_g$ from about $-10°$ C. to $50°$ C. when measured by differential thermal analysis. The instant aqueous emulsion polymer nail coating formulation has the advantages of using water as the solvent so it is non-flammable, of having less occlusion of the nail to permit greater moisture vapor transmission of the nail, of eliminating the toluenesulfonamide formaldehyde resin, and of having a faster drying time than those lacquers of the prior art. The instant nail coating formulation has acceptable adherence to the keratin, gloss, viscosity, and durability.

Some of the prior art concerning cosmetic film forming compositions is discussed below.

The zinc-complex formulation disclosed in *Chemical Week*, 154 (June 21, 1969), is a zinc cross-linked formulation with a Carboset ® (acrylic polymer). This formulation is an aqueous solution with the disadvantages of softening on contact with water, a rather low solids content, and poor resistance to alkali.

U.S. Pat. No. 2,887,116 discloses an aqueous polymer system; however, the polymers employed are water-dispersible hydrophilic ionic organic nitrogenous polymers in a liquid diluent, used as a base coat.

U.S. Pat. No. 3,697,644 discusses an emulsion polymer system which has an organic solvent and the polymer is dissolved in organic liquid droplets. The utility of the emulsion is to coat the skin or hair.

U.S. Pat. No. 3,639,572 discloses a water-resistant liquid makeup for eyelids. The emulsion polymer for this purpose is at a neutral pH and very dilute.

British Pat. No. 1,074,201 discloses amine-substituted acrylic emulsion polymers used as nail polishes. The amino nitrogen-containing monomer is 10-100% of the polymer.

French Pat. No. 1,504,440 discloses an acrylic emulsion for application to the skin or hair but the solids content of the final formulation is very low.

U.S. Pat. No. 2,996,432 discloses converting a preformed polymer to an emulsion of a rubber-like latex for use as a facial mask.

Japanese published application No. 75/28502 discloses organic solution polymers which are readily removed. These are non-aqueous systems.

British Pat. No. 1,032,367 discloses an aqueous alkali resistant coating. The polymer is comprised of monomers at least 5 to 25% being a basic amino nitrogen containing monomer. Although several polymer types are discussed, the formulations relate to waxes and other polymer uses.

U.S. Pat. No. 3,927,203 discloses a solution polymer system for cosmetic uses. Although the disclosure purports to contemplate emulsion polymers, it is clear from the disclosure of polymerization conditions and suitable solvents for polymerization that aqueous emulsion polymers of the type employed in the present invention were not visualized. Also, this patent only exemplifies organic solvent systems for the nail lacquer formulations.

SUMMARY OF THE INVENTION

This invention relates to a nail coating formulation which upon drying forms a film which will adhere to keratin of the nail and has a moisture vapor transmission from about 0.1 to about 1.6 mg./cm.$^2$/hr., said formulation comprising an aqueous emulsion polymer having a solids content from about 30 to about 55 percent, the polymer having a $T_g$ within the range of about $-10°$ C. to about $50°$ C. when measured by differential thermal analysis and being prepared by an aqueous emulsion polymerization of two or more of the following monomers, at least one of which is of formula I or formula II;

$$CH_2=CH \quad\quad (I)$$
$$|$$
$$COOR$$

$$CH_2=C-CH_3 \quad\quad (II)$$
$$|$$
$$COOR$$

$$R^1-C=CHR^1 \quad\quad (III)$$

(attached to phenyl ring with R$^2$ substituent)

wherein R is $C_1$-$C_{20}$ alkyl, phenyl, benzyl, hydroxy-($C_1$-$C_4$)-alkyl, $C_1$-$C_4$ alkoxy-($C_1$-$C_4$)alkyl, cyclopentyl, cyclohexyl, furyl, $C_1$-$C_4$ alkylfuryl, tetrahydrofuryl, or $C_1$-$C_4$ alkyltetrahydrofuryl; $R^1$ is hydrogen or methyl; and $R^2$ is hydrogen or $C_1$-$C_3$ alkyl, subject to the limitation that when R in one of the monomers is $C_1$-$C_4$ alkoxy-($C_1$-$C_4$)alkyl, then R in the other monomer is a group other than $C_1$-$C_4$ alkoxy-($C_1$-$C_4$)alkyl or hydroxy-($C_1$-$C_4$)alkyl.

In a preferred group of monomers of the above formulation, R is $C_1$-$C_8$ alkyl and $R^1$ is hydrogen.

The preferred number of monomers is from 2 to 4.

A preferred solids content of the emulsion polymer is from about 35 to about 45 percent.

A preferred $T_g$ range is from about $10°$ to about $30°$ C.

Preferred acrylate monomers, formula I, include 2-ethylhexyl acrylate, ethyl acrylate, and butyl acrylate.

Preferred methacrylate monomers, formula II, include methyl methacrylate and ethyl methacrylate.

Preferred styrene monomers, formula III, include 4-vinyltoluene and styrene.

DETAILED DESCRIPTION OF THE INVENTION

The polymers which are prepared for use in this invention are prepared from two or more of the following monomers, at least one of which is of formula I or formula II;

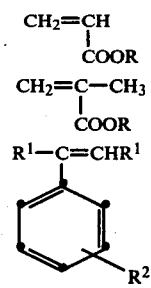

$$CH_2=CH \quad (I)$$
$$\qquad |$$
$$\qquad COOR$$

$$CH_2=C-CH_3 \quad (II)$$
$$\qquad |$$
$$\qquad COOR$$

$$R^1-C=CHR^1 \quad (III)$$

wherein R is $C_1$-$C_{20}$ alkyl, phenyl, benzyl, hydroxy-($C_1$-$C_4$)-alkyl, $C_1$-$C_4$ alkoxy-($C_1$-$C_4$)alkyl, cyclopentyl, cyclohexyl, furyl, $C_1$-$C_4$ alkylfuryl, tetrahydrofuryl, or $C_1$-$C_4$ alkyltetrahydrofuryl; $R^1$ is hydrogen or methyl; and $R^2$ is hydrogen or $C_1$-$C_3$ alkyl, subject to the limitation that when R in one of the monomers is $C_1$-$C_4$ alkoxy-($C_1$-$C_4$)alkyl, then R in the other monomer is a group other than $C_1$-$C_4$ alkoxy-($C_1$-$C_4$)-alkyl or hydroxy-($C_1$-$C_4$)alkyl.

The term "$C_1$-$C_{20}$ alkyl" includes straight and branched-chain isomers of 1 to 20 carbon atoms such as methyl, ethyl, propyl, isopropyl, butyl, isobutyl, tertiary butyl, pentyl, isopentyl, neopentyl, hexyl, isohexyl, heptyl, isoheptyl, octyl, isooctyl, nonyl, decyl, dodecyl, pentadecyl, hexadecyl, octadecyl, eicosyl, 3-methylpentyl, 2,7,8-trimethyldecyl, 4-isobutyl-2,5-dimethylheptyl, 2,3,5-trimethyl-4-propylheptyl, 4-ethyl-5-methyloctyl, 3,3-dimethylbutyl, 2-ethyl-3-methylbutyl, 2,3,4-trimethylpentyl, 2,3,4-trimethyl-5,6-diethyloctyl, 2,3,5,7-tetramethyl-3,4,5,6-tetraethyloctyl, and the like. The terms "$C_1$-$C_8$ alkyl", "$C_1$-$C_4$ alkyl", and "$C_1$-$C_3$ alkyl" are within the above definition of $C_1$-$C_{20}$ alkyl. The term "$C_1$-$C_4$ alkoxy-($C_1$-$C_4$)-alkyl" can also be stated as ($C_1$-$C_4$ alkyl)-O-($C_1$-$C_4$ alkyl) wherein the two $C_1$-$C_4$ alkyl portions are defined within the above $C_1$-$C_{20}$ alkyl term. The term "hydroxy-($C_1$-$C_4$)alkyl" has a hydroxy group on a $C_1$-$C_4$ alkyl group, such as 2-hydroxypropyl, 2-hydroxybutyl, 3-hydroxybutyl, and 2-hydroxy-2-methylpropyl.

Examples of suitable acrylate esters, formula I, are methyl acrylate, ethyl acrylate, butyl acrylate, benzyl acrylate, furyl acrylate, methylfuryl acrylate, butylfuryl acrylate, methoxyethyl acrylate, ethoxyethyl acrylate, 2-ethylhexyl acrylate, cyclopentyl acrylate, cyclohexyl acrylate, 2,3-epoxy-1-propyl acrylate, and lauryl acrylate.

Examples of methacrylate esters, formula II, are methyl methacrylate, ethyl methacrylate, propyl methacrylate, butyl methacrylate, phenyl methacrylate, benzyl methacrylate, propyleneglycol monomethacrylate, stearyl methacrylate, tetrahydrofuryl methacrylate, methyltetrahydrofuryl methacrylate, butyltetrahydrofuryl methacrylate and hydroxyethyl methacrylate.

Examples of suitable styrene monomers, formula III, are styrene, 4-vinyltoluene, 2-vinyltoluene, α-methylstyrene, and 4-isopropylstyrene.

Polymers for commercial or laboratory use are prepared in a number of ways such as by bulk, solution, suspension, or emulsion polymerization. Emulsion polymerization can be carried out in either water or an organic solvent as the continuous phase. This invention uses emulsion polymerization to prepare the polymers, and uses water as the continuous phase. Methods of emulsion polymerization are well known in the art, e.g., Sorensen and Campbell, *Preparative Methods of Polymer Chemistry*, Interscience, 1961, N.Y., pages 127, 162–165, 169, 172, 179, 187, 210, 211, 219, 226 and *Encyclopedia of Polymer Science and Technology*, Volume 5, Interscience, 1966, N.Y., page 801. Generally, aqueous emulsion polymerization involves adding to water a water-soluble catalyst, monomers, and surface-active agent.

More than one surface-active agent may be used, and a combination of anionic and non-ionic surface-active agents is possible. Cationic surface-active agents are rarely used. The anionic and non-ionic surface-active agents are preferred.

Examples of suitable non-ionic surface-active agents are alcohol-ethylene oxide condensates, fatty acid-ethylene oxide condensates, phenol-ethylene oxide condensates, modified alkyl resins, and sorbitol-fatty acid adducts. Preferred non-ionic surface-active agents are phenol-ethylene oxide condensates and modified alkyl resins. Examples of suitable anionic surface-active agents are polyether sulfonates, dialkyl sulfosuccinates, alkyl and alkaryl sulfonates, dialkyl sulfosuccinamides, alkyl sulfates, and phosphate esters, such as those of the formula

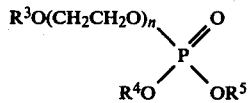

wherein $R^3$ is a $C_1$-$C_4$ alkyl or alkaryl group, $R^4$ is hydrogen, sodium, $C_1$-$C_4$ alkyl, or an alkaryl radical, and $R^5$ is hydrogen or sodium, and n is the average number of units of ethylene oxide. Preferred anionic-surfactants are polyether sulfonates and alkyl sulfonates.

The catalyst which is used may be a non-redox catalyst which is activated by heat, or the catalyst may be a redox catalyst system which does not require heat. All of the components for preparing the polymer may be added initially or some may be added during the polymerization.

Examples of suitable catalysts which can be used in the emulsion polymerization are non-redox catalysts, such as persulfate salts, hydrogen peroxide, and organic peroxides; redox catalysts, such as, sodium bisulfite, sodium metabisulfite, sodium hydrosulfite, sodium thiosulfate, and sodium formaldehyde sulfoxylate. Redox catalysts require an activator, such as ferrous sulfate heptahydrate, and ferrous ammonium sulfate. The preferred catalysts are persulfate salts, sodium formaldehyde sulfoxylate, and ferrous sulfate heptahydrate.

Additional ingredients may be added, but they are not necessary to form an emulsion polymerization. Some examples of such additional ingredients are buffers and additives to control viscosity. The polymerization mixture is stirred under a nitrogen atmosphere and the temperature is controlled to be within the range optimal for the monomers and catalysts used. Thus, the mixture may require heat or cooling.

The monomers are selected and copolymerized in proportions such that the $T_g$ of the resulting copolymer is from about $-10°$ to about $50°$ C. The preferred $T_g$ range is from about $10°$ to about $30°$ C. $T_g$ is the glass transition temperature and is approximately the point at which a polymer changes from being a glass-like material to a rubber-like material. The $T_g$ is a property of the polymer. Since the $T_g$ is not a thermodynamic property, its value will vary somewhat depending upon the method used to measure it, e.g., change in specific heat, refractive index, or density as a function of temperature. For the purposes of this invention $T_g$ is measured by differential thermal analysis.

It is well known in the art of polymer chemistry (see Collins, et al., *Experiments In Polymer Science*, Wiley-Interscience, N.Y., 1973) that amorphous random copolymers exhibit a single $T_g$ which lies between the values of the respective homopolymers. For example, a single $T_g$ can be found for a copolymer by using the following formula $$T_g = \frac{(W_1 T_{g1} + K W_2 T_{g2})}{W_1 + K W_2}$$

where $T_{g1}$ and $T_{g2}$ refer to the glass transition temperatures of two homopolymers present in the weight fractions $W_1$ and $W_2$ (wherein $W_1 + W_2 = 1$), and K is defined by the following formula $$K = \frac{(\alpha_r - \alpha_g)_2}{(\alpha_r - \alpha_g)_1}$$

where $\alpha_r$ represents the thermal-expansion co-efficients of the homopolymers in the rubbery state; and $\alpha_g$ represents the thermal-expansion co-efficients of the homopolymers in the glassy state. Similar formulas to that shown above for $T_g$ can be developed for polymers containing more than two monomers. [See, R. F. Boyer, *Rubber Chem. Technol.* 36(5), 1303–421 (1963)]. Therefore, those skilled in the art can readily select two or more monomers and combine them in suitable proportions to obtain a polymer with the desired $T_g$.

Another important property of the polymer films used as nail coatings is their moisture vapor transmission (MVT). This MVT property refers to the ability of the finger (nail bed) to transmit water through the nail and polymer film. In vivo measurements of MVT have been discussed by David Spruit, *American Cosmetics and Perfumery*, 87, 57–58 (1972). The author states that the water vapor loss from a healthy, human middle fingernail was found to be 1.6 mg./cm.$^2$/hr. The fingernail covered in vivo with a 0.03 or 0.07 mm. thickness of nail polish (a commercial preparation, Miss Helen TM) had the water vapor transmission reduced to 0.40 mg./cm.$^2$/hr. Therefore, the presence of a nail lacquer impedes the water loss and increases the hydration of the nail as the structure of the nail plate is highly permeable. In vitro measurements of MVT have been done using a modified apparatus and method originally described by George E. Buch and Travis Winsor, *Archives of Dermatology and Syphilology*, 53, 39–41 (1946). This modified apparatus is discussed hereinafter. The following table shows the vapor film transmissions found using commercially available nail lacquers for the in vitro test discussed in the Burch article which than can be compared with the in vivo test discussed in the Spruit article.

| Polymer | Average Thickness mm. | Transmission mg./cm.$^2$/hr. |
|---|---|---|
| Elizabeth Arden ® Natural | 0.07 | 0.4 |
| Elizabeth Arden ® Natural | 0.17 0.1 | |
| Miss Helen$^{TM}$ | 0.05 | 0.4 |
| None | None | 1.6 |

From the above results it can be seen that one coat of Elizabeth Arden ® Natural, first entry in the table, resulted in a transmission of 0.4 mg./cm.$^2$/hr. by the in vitro test employed. This result compared favorably with the in vivo test of Miss Helen TM in the article where the transmission result was 0.4 mg./cm.$^2$/hr. Therefore, the above mentioned results for the emulsion polymer formulations of this invention when measured for vapor transmission can be done by an in vitro test with results within the same range as would be expected with an in vivo test. These results are given later.

Based on the above known test results the MVT should desirably be from about 0.1 to 1.6 mg./cm.$^2$/hr. By combining the $T_g$ property of a polymer with the moisture vapor transmission (MVT) parameter, it is possible to obtain a nail coating of superior properties. Stated another way, depending on the particular properties desired in the polymer, it is possible to select monomers that will yield polymers within the given range of $T_g$ which when used as nail coatings will have an acceptable MVT for a particular application.

The emulsion polymers used in the present formulations should have a solids content from about 30 to about 55 percent, with a preferred range of from about 35 to about 45 percent. The solids content can be lower, but too low a solids content is simply not economical. To obtain the optimum thickness of the coating on the nail, the higher solids content is preferred. If the solids content goes above 50 percent, viscosity increases rapidly and the viscosity will then be too high to result in a suitable product.

In addition to the above three classes of monomers, formulae I, II and III, additional optional monomers may be present; however, the total amount of any of the optional monomers should not exceed 10 percent by weight and should preferably be less than 5 percent by weight. The specific nature of the optional monomer is not critical so long as the amount of any optional monomer added is such that the $T_g$ of the final polymer is within the range from about $-10°$ C. to 50° C. and the moisture vapor transmission is from 0.1 to 1.6 mg./cm.$^2$/hr.

One possible optional monomer class is of the general formula

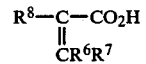

wherein $R^6$ is hydrogen or methyl, $R^7$ is hydrogen, methyl, or carboxy, $R^8$ is hydrogen, methyl, or carboxymethyl, and the mono- or dicarboxylic acid esters thereof. Examples of such acidic monomers of this class are maleic acid, citraconic acid, crotonic acid, allylacetic acid, acrylic acid, methacrylic acid, itaconic acid, monomethyl itaconate, dibutyl maleate, dibutyl itaconate and the like. A preferred optional monomer is methacrylic acid.

A second optional monomer class is basic monomers. The basic monomers will, of course contain at least one grouping such as

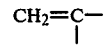

group and will, in addition contain a basic nitrogen. Examples of such basic monomers are 2-vinylpyridine, 4-vinylpyridine, 2-allyloxypyridine, dimethylaminoethyl acrylate, dimethylaminoethyl methacrylate, t-butylaminoethyl methacrylate and the like.

A third class of optional monomers is alkenyl monomers and includes vinyl acetate, vinyl chloride, vinylidene chloride, acrylonitrile and the like.

Another possible class of optional monomers which may be present is cross linking agents. These cross linking agents are of the formula

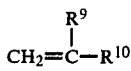

wherein $R^9$ is hydrogen or methyl, and $R^{10}$ contains at least one of the following groups:

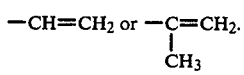

Examples of suitable cross linking agents are ethylene diacrylate, divinylbenzene, trivinylbenzene, divinylsulfone, vinyl acrylate, bisphenol A dimethacrylate, pentaerythritol tetramethacrylate, and 1,1,1-trimethylolpropane trimethacrylate.

Although mixtures of the above optional monomers may be used, in any one polymer system the acidic monomer and basic monomer are not used simultaneously.

The amount of any optional monomers added is such that the $T_g$ of the final polymer is within the above-described desired range. Compensation for changes of the $T_g$ because of the addition of the various optional components must be made, using appropriate formulae referred to hereinabove, to maintain the $T_g$ within the given range.

Because the requirements of a nail lacquer base-coat, color-coat or top-coat may be different the monomers are selected accordingly. The presence of the optional monomers, discussed hereinbefore, allow for further refinement of the properties of the final polymer. The most important property of the final polymer is a $T_g$ within the desired range of from about $-10°$ to about $55°$ C.

The nail coating formulation consists of at least the emulsion polymer used as a clear coating. Often additional optional ingredients are added such as pigments, dyes, dispersing agents, wetting agents, thickeners, coalescing agents, preservatives, antifoams, chelating agents, buffers, and UV absorbers. The selection of such optional ingredients is well within the skill of those familiar with the cosmetic art.

If a pigment or dye is used, it should be relatively light-fast and nonbleeding. Pearlescent substances, such as mica, guanine, bismuth oxychloride, or titanium dioxide on mica can also be used. Many examples of suitable pigments and dyes are given by Madison G. deNavarre, The Chemistry and Manufacture of Cosmetics, 4, 996–998 (2nd ed).

Dispersing agents and wetting agents are often used as surfactants in these nail coating formulations to help disperse uniformly the pigment. Inorganic pigments are naturally hydrophylic and are easily dispersed in an aqueous emulsion system. Organic pigments are hydrophobic and will require a dispersing agent or wetting agent to reduce the surface tension and permit uniform dispersion. A listing of suitable surfactants is given in *Encyclopedia of Chemical Technology*, Surfactants, 19, 584 (1969), from which those skilled in the art will readily choose appropriate agents.

Thickeners are added to prevent separation and settling. Suitable thickeners can be selected from among natural gums, such as guar, gum arabic, cellulose, cellulose derivatives and the like; silicates, such as V-gum ® and the like; clays, such as stearylkonium hectorite and the like; and synthetic polymers, such as acrylates, e.g., Carbopol ®, Acrysols ® and the like.

Coalescing agents can be added to lower the temperature at which the film can form. Thus, the coalescing agents serve a function only during film formation. For the purposes of this invention these agents must be water soluble. One class of suitable coalescing agents includes the glycol ethers, such as ethylene glycol monobutyl ether, diethylene glycol monomethyl ether, propylene glycol monomethyl ether, dipropylene glycol monomethyl ether and the like.

Preservatives are frequently used to prevent bacterial and fungal growth during storage of the nail coating formulations. Commonly used preservatives such as the ($C_1$-$C_6$ alkyl)-p-hydroxybenzoic acid esters, such as methyl p-hydroxybenzoate, ethyl p-hydroxybenzoate, butyl p-hydroxybenzoate, hexyl p-hydroxybenzoate and the like; organic salts, such as potassium sorbate and the like; inorganic salts, such as salts of mercury and the like; and formaldehyde and formaldehyde releasing compounds can be employed.

Antifoams can be used to prevent foam and bubbles during manufacturing and application to the nail. Examples of suitable antifoams are silicone compounds, such as substituted silicones, e.g., methyl silicone or dimethyl silicone, silica, silicon/silica mixture and the like; and poloxyethylene/polyoxypropylene condensates.

Chelating agents remove heavy metal ions which may affect the stability of the nail lacquer formulation. Suitable chelating agents are ethylenediamine tetraacetic acid (EDTA) and its mono or tetra sodium salt, tetrasodium pyrophosphate and the like.

The nail coating formulation is buffered, when necessary, to have a pH 7-10, and preferably pH $8.0\pm0.5$.

UV absorbers are used to prevent UV radiation from deteriorating the polymer, fading the pigment or dye, and making brittle the nail coating film. A listing of suitable UV absorbers is given in *Encyclopedia of Chemical Technology*, UV Absorbers, 21, 115–122 (1969).

Emulsion Polymer Examples

In the following examples of the preparation of emulsion polymers, all $T_g$ values were determined on a Du Pont ® 990 Thermal Analyzer using glass beads as the reference. The thermocouple was painted with the emulsion, air-dried for 24 hours, then dried in vacuo at $25°$ C. for 48 hours. The system was then cooled to $-80°$ C. with liquid nitrogen, then heated at a rate of $10°$ C. per minute and the $T_g$ was taken as the first departure from the base line.

The solids content was determined by pipetting 5.0 ml. of the emulsion into a tared aluminum dish. The emulsion in the dish was air-dried for 24 hours, dried in vacuo for 24 hours at $25°$ C., and then dried 24 hours at $50°$ C. The residue was cooled in a dessicator and then weighed to determine the solids content.

The following examples illustrate the preparation of the emulsion polymers of this invention, but these examples are for illustrative purposes only and are not to be construed as limiting.

EXAMPLE 1

Sodium dodecyl sulfate (2.9 g.) and 177 ml. of water were added to a 500 ml. reaction vessel equipped with a tachometer stirrer. A monomer mixture of 48.0 g. of methyl methacrylate, 48.0 g. of 2-ethylhexyl acrylate, 2.0 g. of methacrylic acid, and 2.0 g. of 1,1,1-trimethylolpropane trimethacrylate was prepared. Stirring was started at 400 rpm. One third of the monomer mixture was initially added to the vessel, with nitrogen bubbling through the solution for 30 min. The reaction mixture was heated to 30° C. The nitrogen bubbler was raised and the reaction mixture was then covered with nitrogen, 0.5 g. of $(NH_4)_2S_2O_8$ in 5 ml. of water was added, and then 0.5 g. of $NaHSO_3$ in 5 ml. of water was added. To this reaction mixture was slowly added the remaining monomer mixture at a rate which required approximately 105 minutes to complete the addition. After an induction period of 12 minutes after beginning the addition of the remaining monomer mixture, the reaction became exothermic, reaching a maximum temperature of 43° C. in an additional 30 minutes. Monomer addition to the reaction mixture continued and the reaction mixture was then heated to a temperature of 60° C. at a rate of approximately a 5° C. increase every 15 minutes. The temperature was kept at 60° C. until the monomer mixture addition was completed, then the emulsion was heated to 90° C. and kept at this temperature for 30 minutes. The reaction mixture was air-cooled to 50° C. and further cooled to 25° C. with an ice/water bath. The cool emulsion was adjusted to pH 8.0 with 28 percent ammonium hydroxide. The pH-adjusted emulsion was filtered through cheesecloth. The emulsion had a solids content of 35.7 percent, and the polymer had a $T_g$ of 3° C.

EXAMPLE 2

When the procedure of Example 1 was repeated using 2.9 g. of sodium dodecyl sulfate, 177 ml. of water, 47.0 g. of methyl methacrylate, 46.0 g. of 2-ethylhexyl acrylate, 2.0 g. of acrylic acid, 5.0 g. of 1,1,1-trimethylolpropane trimethacrylate, 0.5 g. of $(NH_4)_2S_2O_8$ in 5 ml. of water, and 0.5 g. of $NaHSO_3$ in 5 ml. of water, the reaction mixture became exothermic after an induction period of 23 minutes and reached a maximum temperature of 50° C. in another 8 minutes. The emulsion had a solids content of 35.3 percent, and the polymer had a $T_g$ of 0° C.

EXAMPLE 3

When the procedure of Example 1 was repeated using 2.9 g. of sodium dodecyl sulfate, 177 ml. of water, 45.0 g. of vinyltoluene (isomeric mixture), 20.0 g. of ethyl acrylate, 32.0 g. of butyl acrylate, 3.0 g. of methacrylic acid, 0.5 g. of $(NH_4)_2S_2O_8$ in 5 ml. of water, and 0.5 g. of $NaHSO_3$ in 5 ml. of water, the reaction became exothermic after an induction period of 2 minutes and reached a maximum temperature of 41° C. in another 18 minutes. The emulsion had a solids content of 35.5 percent, and the polymer had a $T_g$ of 14° C.

EXAMPLE 4

When the procedure of Example 1 was repeated using 7.4 g. of sodium alkylaryl polyether sulfonate (Triton X-200, Rohm and Haas), 11.0 g. of alkylaryl polyether alcohol (OPE 30, Rohm and Haas), 174 ml. of water, 127.6 g. of methyl methacrylate, 85.8 g. of 2-ethylhexyl acrylate, 6.6 g. of methacrylic acid, 1.1 g. of $(NH_4)_2S_2O_8$ in 10 ml. of water, and 1.1 g. of $NaHSO_3$ in 10 ml. of water, the reaction became exothermic after an induction period of 22 minutes and reached a maximum temperature of 67° C. in another 6 minutes. The emulsion had a solids content of 54.2 percent, and the polymer had a $T_g$ of 12° C.

EXAMPLE 5

When the procedure of Example 1 was repeated using 2.9 g. of sodium dodecyl sulfate, 177 ml. of water, 58.5 g. of ethyl methacrylate, 38.5 g. of butyl acrylate, 3.0 g. of methacrylic acid, 0.5 g. of $(NH_4)_2S_2O_8$ in 5 ml. of water, and 0.5 g. of $NaHSO_3$ in 5 ml. of water, the reaction became exothermic after an induction period of 23 minutes and reached a maximum temperature of 50° C. in another 13 minutes. The emulsion had a solids content of 36.2 percent, and the polymer had a $T_g$ of 7° C.

EXAMPLE 6

When the procedure of Example 1 was repeated using 2.9 g. of sodium dodecyl sulfate, 177 ml. of water, 68.5 g. of ethyl methacrylate, 28.5 g. of 2-ethylhexyl acrylate, 3.0 g. of methacrylic acid, 0.5 g. of $(NH_4)_2S_2O_8$ in 5 ml. of water, and 0.5 g. of $NaHSO_3$ in 5 ml. of water, the reaction became exothermic after an induction period of 37 minutes and reached a maximum temperature of 54° C. in another 11 minutes. The emulsion had a solids content of 36.4 percent, and the polymer had a $T_g$ of 3° C.

EXAMPLE 7

When the procedure of Example 1 was repeated using 2.9 g. of sodium dodecyl sulfate, 177 ml. of water, 65.0 g. of methyl methacrylate, 32.0 g. of butyl acrylate, 3.0 g. of methacrylic acid, 0.5 g. of $(NH_4)_2S_2O_8$ in 5 ml. of water, and 0.5 g. of $NaHSO_3$ in 5 ml. of water, the reaction became exothermic after an induction period of 8 minutes and reached a maximum temperature of 44° C. in another 23 minutes. The emulsion had a solids content of 35.5 percent, and the polymer had a $T_g$ of 35° C.

EXAMPLE 8

When the procedure of Example 1 was repeated using 2.9 g. of sodium dodecyl sulfate, 177 ml. of water, 50.0 g. of methyl methacrylate, 43.0 g. of 2-ethylhexyl acrylate, 5.0 g. of di-n-butyl itaconate, 2.0 g. of acrylic acid, 0.5 g. of $(NH_4)_2S_2O_8$ in 5 ml. of water, and 0.5 g. of $NaHSO_3$ in 5 ml. of water. The reaction became exothermic after an induction period of 3 minutes and reached a maximum temperature of 43° C. in another 7 minutes. The emulsion had a solids content of 35.6 percent, and the polymer had a $T_g$ of 2° C.

EXAMPLE 9

When the procedure of Example 1 was repeated using 2.9 g. of sodium dodecyl sulfate, 177 ml. of water, 56.5 g. of ethyl methacrylate, 38.5 g. of butyl acrylate, 5.0 g. of monomethyl itaconate, 0.5 g. of $(NH_4)_2S_2O_8$ in 5 ml. of water, and 0.5 g. of $NaHSO_3$ in 5 ml. of water, the reaction became exothermic after an induction period of 1 minute and reached a maximum temperature of 41° C. in another 5 minutes. The emulsion had a solids content of 35.7 percent, and the polymer had a $T_g$ of 8° C.

EXAMPLE 10

When the procedure of Example 1 was repeated using 2.9 g. of sodium dodecyl sulfate, 177 ml. of water, 30.0 g. of methyl methacrylate, 30.0 g. of styrene, 33.0 g. of 2-ethylhexyl acrylate, 5.0 g. of dibutyl maleate, 2.0 g. of methacrylic acid, 0.5 g. of $(NH_4)_2S_2O_8$ in 5 ml. of water, and 0.5 g. of $NaHSO_3$ in 5 ml. of water, the reaction never became exothermic. The temperature of the reaction mixture was then increased 5° C. every 15 minutes until reaching 60° C. when the emulsion formed. The emulsion had a solids content of 35.6 percent, and the polymer had a $T_g$ of 13° C.

EXAMPLE 11

When the procedure of Example 1 was repeating using 2.9 g. of sodium dodecyl sulfate, 177 ml. of water, 28.0 g. of methyl methacrylate, 20.0 g. of α-methyl styrene, 40.0 g. of 2-ethylhexyl acrylate, 10.0 g. of dibutyl maleate, 2.0 g. of methacrylic acid, 0.5 g. of $(NH_4)_2S_2O_8$ in 5 ml. of water, and 0.5 g. of $NaHSO_3$ in 5 ml. of water, the reaction never became exothermic. The temperature of the reaction mixture was increased 5° every 15 minutes until reaching 60° C. where the emulsion formed. The emulsion had a solids content of 34.4 percent, and the polymer had a $T_g$ of 4° C.

EXAMPLE 12

When the procedure of Example 1 was repeated using 2.9 g. of sodium dodecyl sulfate, 177 ml. of water, 30.0 g. of methyl methacrylate, 30.0 g. of styrene, 38.0 g. of 2-ethylhexyl acrylate, 2.0 g. of methacrylic acid, 0.5 g. of $(NH_4)_2S_2O_8$ in 5 ml. of water, and 0.5 g. of $NaHSO_3$ in 5 ml. of water, the reaction became exothermic after an induction period of 3 minutes and reached a maximum temperature of 38° C. in another 40 minutes. The emulsion had a solids content of 34.7 percent, and the polymer had a $T_g$ of 9° C.

EXAMPLE 13

When the procedure of Example 1 was repeated using 2.9 g. of sodium dodecyl sulfate, 177 ml. of water, 50.0 g. of methyl methacrylate, 48.0 g. of butyl acrylate, 2.0 g. of methacrylic acid, 0.25 g. of ethylene diacrylate, 0.5 g. of $(NH_4)_2S_2O_8$ in 5 ml. of water, and 0.5 g. of $NaHSO_3$ in 5 ml. of water, the reaction mixture became exothermic after an induction period of 7 minutes and reached a maximum temperature of 46° in another 13 minutes. The emulsion had a solids content of 35.7 percent, and the polymer had a $T_g$ of 0° C.

EXAMPLE 14

When the procedure of Example 1 was repeated using 2.9 g. of sodium dodecyl sulfate, 177 ml. of water, 48.0 g. of methyl methacrylate, 48.0 g. of butyl acrylate, 2.0 g. of methacrylic acid, 2.0 g. of ethylene diacrylate, 0.5 g. of $(NH_4)_2S_2O_8$ in 5 ml. of water, and 0.5 g. of $NaHSO_3$ in 5 ml. of water, the reaction became exothermic after an induction period of 22 minutes and reached a maximum temperature of 49° C. in another 24 minutes. The emulsion had a solids content of 35.7 percent, and the polymer had a $T_g$ of 19° C.

EXAMPLE 15

When the procedure of Example 1 was repeated using 2.9 g. of sodium dodecyl sulfate, 177 ml. of water, 35.0 of methyl methacrylate, 33.0 g. of butyl acrylate, 30.0 g. of cyclohexyl acrylate, 2.0 g. of methacrylic acid, 0.5 g. of $(NH_4)_2S_2O_8$ in 5 ml. of water, and 0.5 g. of $NaHSO_3$ in 5 ml. of water, the reaction became exothermic after an induction period of 1 minute and reached a maximum temperature of 47° C. in another 6 minutes. The emulsion had a solids content of 35.5 percent, and the polymer had a $T_g$ of 11° C.

EXAMPLE 16

When the procedure of Example 1 was repeated using 2.9 g. of sodium dodecyl sulfate, 177 ml. of water, 55.0 g. of methyl methacrylate, 13.0 g. of 2-ethylhexyl acrylate, 30.0 g. of 2-methoxyethyl acrylate, 2.0 g. of methacrylic acid, 0.5 g. of $(NH_4)_2S_2O_8$ in 5 ml. of water, and 0.5 g. of $NaHSO_3$ in 5 ml. of water, the reaction became exothermic after an induction period of 11 minutes and reached a maximum temperature of 45° C. in another 18 minutes. The emulsion had a solids content of 36.2 percent, and the polymer had a $T_g$ of 13° C.

EXAMPLE 17

When the procedure of Example 1 was repeated using 2.9 g. of sodium dodecyl sulfate, 177 ml. of water, 35.0 g. of methyl methacrylate, 48.0 g. of butyl acrylate, 15.0 g. of phenyl methacrylate, 2.0 g. of methacrylic acid, 0.5 g. of $(NH_4)_2S_2O_8$ in 5 ml. of water, and 0.5 g. of $NaHSO_3$ in 5 ml. of water, the reaction became exothermic after an induction period of 34 minutes and reached a maximum temperature of 57° C. in another 11 minutes. The emulsion had a solids content of 35.7 percent, and the polymer had a $T_g$ of 0° C.

EXAMPLE 18

Sodium dodecyl sulfate (2.0 g.), 6.0 g. of alkylaryl polyether alcohol (1:40 octylphenol:ethylene oxide condensate; Triton X-405, Rohm and Haas), and 180 ml. of water were added to a 500 ml. reaction vessel equipped with a tachometer stirrer. A monomer mixture of 45.0 g. of methyl methacrylate, 54.0 g. of ethyl acrylate, and 1.0 g. of 4-vinylpyridine was added to the vessel. The reaction mixture was stirred at 400 rpm and nitrogen was bubbled through the mixture for 30 minutes. The mixture was cooled to 20° C. with an ice/water bath, and the mixture was then covered with nitrogen. To the reaction mixture was added sequentially 2.0 ml. of a 0.15 percent ferrous sulfate solution, 0.5 g. of $(NH_4)_2S_2O_8$ in 5 ml. of water, and 0.35 g. of sodium formaldehyde sulfoxylate in 5 ml. of water. The reaction became exothermic after an induction period of 12 minutes and reached a maximum temperature of 76° C. in another 14 minutes. Five minutes after the maximum temperature was reached, 0.2 ml. of t-butyl hydroperoxide was added to the vessel, and the emulsion was heated to 75° C. and kept at that temperature for 30 minutes. The emulsion was air-cooled to 50° C., then cooled to 25° C. with an ice/water bath, and filtered through cheesecloth. The emulsion had a solids content of 35.9 percent, and the polymer had a $T_g$ of 4° C.

EXAMPLE 19

When the procedure of Example 18 was repeated using 3.4 g. of sodium alkylaryl polyether sulfonate (Triton X-200, Rohm and Hass), 180 ml. of water, 50.0 g. of methyl methacrylate, 47.0 g. of butyl acrylate, 3.0 g. of itaconic acid, 10.0 ml. of a 0.15 percent ferrous sulfate solution, 0.5 g. of $(NH_4)_2S_2O_8$ in 5 ml. of water, and 0.35 g. of sodium formaldehyde sulfoxylate in 5 ml. of water, the reaction became exothermic after an induction period of less than 1 minute and reached a maximum temperature of 61° C. in another 10 minutes. The cooled emulsion was neutralized to pH 8.0 with 28 percent ammonium hydroxide. The solids content of the emulsion was 32.2 percent, and the polymer had a $T_g$ of 11° C.

EXAMPLE 20

When the procedure of Example 18 was repeated using 3.4 g. of sodium alkylaryl polyether sulfonate (Triton X-200, Rohm and Haas), 180 ml. of water, 50.0 g. of methyl methacrylate, 48.0 g. of butyl acrylate, 2.0 g. of crotonic acid, 10.0 ml. of a 0.15 percent ferrous sulfate solution, 0.5 g. of $(NH_4)_2S_2O_8$ in 5 ml. of water, and 0.35 g. of sodium formaldehyde sulfoxylate in 5 ml. of water, the reaction became exothermic after an induction period of 1 minute and reached a maximum temperature of 60° C. in another 8 minutes. The cooled emulsion was neutralized to pH 8.0 with 28 percent ammonium hydroxide. The emulsion had a solids content of 31.9 percent, and the polymer had a $T_g$ of 2° C.

EXAMPLE 21

When the procedure of Example 18 was repeated using 3.4 g. of sodium alkylaryl polyether sulfonate, (Triton X-200, Rohm and Haas), 197 ml. of water, 45.0 g. of methyl methacrylate, 45.0 g. of butyl acrylate, 10.0 g. of hydroxyethyl methacrylate, 1.0 g. of acrylic acid, 10.0 ml. of a 0.15 percent ferrous sulfate solution, 0.5 g. of $(NH_4)_2S_2O_8$ in 5 ml. of water, and 0.35 g. of sodium formaldehyde sulfoxylate in 5 ml. of water, the reaction became exothermic after an induction period of less than 1 minute and reached a maximum temperature of 65° C. in another 7 minutes. The cooled emulsion was neutralized to pH 8.0 with 28 percent ammonium hydroxide. The emulsion had a solids content of 32.1 percent, and the polymer had a $T_g$ of 3° C.

EXAMPLE 22

When the procedure of Example 18 was repeated using 2.0 g. of sodium dodecyl sulfate, 6.0 g. of alkylaryl polyether alcohol (1:40 octylphenol:ethylene oxide condensate; Triton X-405, Rohm and Haas), 180 ml. of water, 44.0 g. of methyl methacrylate, 51.0 g. of ethyl acrylate, 5.0 g. of dimethylaminoethyl methacrylate, 2.0 ml. of a 0.15 percent ferrous sulfate solution, 0.5 g. of $(NH_4)_2S_2O_8$ in 5 ml. of water, and 0.35 g. of sodium formaldehyde sulfoxylate in 5 ml. of water, the reaction became exothermic after an induction period of 3 minutes and reached a maximum temperature of 69° C. in another 11 minutes. The emulsion had a solids content of 35.2 percent, and the polymer had a $T_g$ of −9° C.

EXAMPLE 23

When the procedure of Example 18 was repeated using 2.0 g. of sodium dodecyl sulfate, 6.0 g. of alkylaryl polyether alcohol (1:40 octylphenol:ethylene oxide condensate; Triton X-405, Rohm and Haas), 45.0 g. of methyl methacrylate, 53.0 g. of ethyl acrylate, 2.0 g. of t-butylaminoethyl methacrylate, 2.0 ml. of a 0.15 percent ferrous sulfate solution, 0.5 g. of $(NH_4)_2S_2O_8$ in 5 ml. of water, and 0.35 g. of sodium formaldehyde sulfoxylate in 5 ml. of water, the reaction became exothermic after an induction period of 20 minutes and reached a maximum temperature of 53° C. in another 65 minutes. The emulsion had a solids content of 35.4 percent, and the polymer had a $T_g$ of 0° C.

EXAMPLE 24

When the procedure of Example 18 was repeated using 5.0 g. of alkylaryl polyether alcohol (1:30 octylphenol:ethylene oxide condensate; Triton X-305, Rohm and Hass), 180 ml. of water, 40.0 g. of methyl methacrylate, 38.0 g. of butyl acrylate, 20.0 g. of tetrahydrofurfuryl methacrylate, 2.0 g. of acrylic acid, 2.0 ml. of a 0.15 percent ferrous sulfate solution, 0.5 g. of $(NH_4)_2S_2O_8$ in 5 ml. of water, and 0.35 g. of sodium formaldehyde sulfoxylate in 5 ml. of water, the reaction became exothermic after an induction period of 1 minute and reached a maximum temperature of 61° C. in another 8 minutes. The cooled emulsion was neutralized to pH 8.0 with 28 percent ammonium hydroxide. The emulsion had a solids content of 34.9 percent, and the polymer had a $T_g$ of 2° C.

EXAMPLE 25

Alkylaryl polyether alcohol (1:30 octylphenol:ethylene oxide condensate; Triton X-305, Rohm and Haas) (2.8 g.) and 120 ml. of water were added to a 500 ml. reaction vessel equipped with a stirrer. A monomer mixture of 31.8 g. of ethyl methacrylate, 19.1 g. of ethyl acrylate, and 2.7 g. of methacrylic acid was added to the vessel with stirring. Nitrogen was bubbled through the mixture for 30 minutes. The mixture was cooled to 20° C. and 1.0 ml. of a 0.15 percent ferrous sulfate solution, 0.25 g. of $(NH_4)_2S_2O_8$ in 2.5 ml. of water, and 0.175 g. of sodium formaldehyde sulfoxylate in 2.5 ml. of water were added, respectively, to the reaction mixture with nitrogen bubbled through. The reaction became exothermic after an induction period of 3 minutes and reached a maximum temperature of 56° C. in another 8 minutes. Five minutes after the maximum temperature was reached, the emulsion was cooled to 25° C. with an ice/water bath. Alkylaryl polyether alcohol (Triton X-305; Rohm and Haas) (3.1 g.), 37.0 g. of ethyl methacrylate, 22.0 g. of ethyl acrylate, 0.5 g. of methacrylic acid, 1.0 ml. of a 0.15 percent ferrous sulfate solution, 0.25 g. of $(NH_4)_2S_2O_8$ in 2.5 ml. of water, 0.175 g. of sodium formaldehyde sulfoxylate in 2.5 ml. of water, and 2 drops of t-butyl hydroperoxide were added, respectively, to the mixture. The reaction was exothermic after an induction period of 1 minute and reached a maximum temperature of 59° C. in another 5 minutes. The emulsion generally cooled to 45° C., and then the emulsion was further cooled to 20° C. with an ice/water bath. The emulsion was filtered through cheesecloth. The emulsion had a solids content of 47.7 percent, and the polymer had a $T_g$ of 0° C.

Moisture Vapor Transmission Examples

The equipment used for performing the MVT measurements is a modification of the apparatus and method described by George E. Burch and Travis Winsor, *Archives of Dermatology and Syphilology*, 53, 39–41 (1946). The apparatus described in this reference has been modified in that a Teflon ® washer without pins replaces the brass ring with pins (for obtaining a tight seal) and a glass liner for the cylinder (for ease in cleaning) has been added.

The vapor transmission of the nail coatings is determined by measuring the rate of diffusion in water (mg./cm.$^2$/hr.) through the film. This rate is measured for the various polymer films of this invention by casting a film at a thickness from 0.05 mm. to 0.20 mm. and mounting the resulting film on the modified apparatus discussed below.

In essence, the apparatus comprises a small steel cylindrical container, externally threaded at the open end to receive an internally threaded cap having in its top an opening of the same dimensions as the opening of the container. The steel container holds a glass liner into which a suitable quantity of water is placed. The film being tested is disposed across the opening in the cylinder so as to cover the entire opening, a Teflon ® washer is placed over the film to insure a tight seal and protect the film when the cap is secured, and the cap is then screwed into place to effect a tight seal between the film and the container. The entire apparatus is immediately weighed to establish a base weight and is then weighed daily for three to four days to determine the weight loss occasioned by the transmission of moisture through the film. Between weighings, the apparatus is stored in an environment having 35%±5% humidity at a temperature of 24° C.±2° C. Given the known area of the opening in the container and time interval over which weight measurements are taken, MVT can readily be calculated in terms of mg./cm.$^2$/hr.

The polymer film to be tested is cast by pouring the emulsion polymer onto a circular Teflon ® plate. In order to define a specific area within which the film will be formed and to insure uniformity of thickness of the film, a steel ring of appropriate size is placed atop the plate and secured thereto by any appropriate means so as to provide a leakproof seal between the Teflon ® plate and the ring. An appropriate quantity of the emulsion polymer is weighed onto the Teflon ® plate to provide the desired film thickness. Since the film thickness for a given area will be determined by the amount of emulsion polymer employed and the solids content of the emulsion polymer, the quantity of emulsion polymer required to provide a film of desired thickness is readily determined. In general, a quantity of 1.5 gm. of an emulsion polymer having a solids content of 35% will yield a film approximately 0.15 mm. in thickness when cast onto a plate having a defined area of 7 cm.$^2$. For emulsion polymers having a solids content other than 35%, the thickness of the film can be predicted by assuming a linear relationship between solids content and film thickness. If necessary to insure complete coverage of the defined surface of the Teflon ® plate, the emulsion polymer placed thereon can be diluted with water as required. The polymer emulsion is then dried to a film by placing the casting unit with the emulsion into a drying oven at 50° C. for at least 8 hours. The dried film is peeled from the Teflon ® plate while still warm and can be used immediately or reserved for future use. The film is cut while at a temperature of 40°–50° C. to a size equal to that of the Teflon ® washer used with the apparatus employed to measure MVT.

The moisture vapor transmission (MVT) results are shown in the following table.

| Polymer of Example No. | Average Thickness mm. | Transmission mg./cm$^2$/hr. |
| --- | --- | --- |
| 1 | 0.15 | 0.5 |
| 2 | 0.15 | 1.2 |
| 3 | 0.15 | 0.2 |
| 5 | 0.14 | 0.7 |
| 6 | 0.15 | 1.4 |
| 9 | 0.18 | 0.7 |
| 10 | 0.13 | 0.2 |
| 11 | 0.13 | 0.2 |
| 12 | 0.12 | 0.2 |
| 13 | 0.06 | 0.6 |
| 14 | 0.10 | 0.6 |
| 15 | 0.15 | 0.4 |
| 16 | 0.13 | 0.8 |
| 17 | 0.18 | 0.3 |
| 19 | 0.11 | 1.0 |
| 20 | 0.14 | 0.5 |
| 21 | 0.12 | 1.6 |
| 22 | 0.15 | 0.8 |
| 23 | 0.10 | 1.3 |
| 24 | 0.12 | 1.3 |
| 25 | 0.11 | 0.9 |

Nail Coating Formulation Examples

The apparatus used in the preparation of many of the following formulations is: a colloid mill [such as a Gifford-Wood ® Homo-mixer made by Gifford-Wood, Inc., Hudson, New York, and labeled Eppenbach TM Homo-mixer], or an Osterizer ® blender [made by John Oster Manufacturing Co.], or a paddle mixer [such as a Lightnin' ® Mixer made by Mixing Equipment Co., Inc., Rochester, N.Y.].

EXAMPLE 26

The color concentrate for the nail coating was prepared from the following ingredients:

| Ingredients | Percent by Weight |
| --- | --- |
| Iron oxide, synthetic brown | 33.33 |
| Tamol ® Rohm and Haas, 731 (25 percent) (sodium salt of carboxylated polyelectrolyte) | 0.63 |
| Triton ®, Rohm and Haas, CF 10 (ethoxylated benzyl ether of octylphenol) | 0.50 |
| Deionized water | 65.54 |
| | 100.00 |

The color concentrate was formed by adding the second and third ingredient in the above listing to the fourth ingredient in an Osterizer ® blender and mixing well. The first ingredient was then slowly added with mixing and scraping of the sides of the blender until all ingredients were smoothly dispersed.

The thickener for the coating formulation was prepared from the following ingredients:

| Ingredients | Percent by Weight |
| --- | --- |
| Natrosol ®, Hercules, 250 M (hydroxyethylcellulose) | 2.00 |
| Deionized water | 78.83 |
| Methyl paraben (methyl p-hydroxybenzoate) | 8.50 |
| Potassium sorbate | 10.00 |
| EDTA . Na$_4$ (sodium ethylenediaminetetraacetic acid) | 0.67 |
| | 100.00 |

The thickener was prepared by heating the water to 80° C. and adding the third, fourth, and fifth ingredients above with stirring until they dissolved. The first ingredient was then dispersed in the mixture at 80° C. with a Gifford-Wood ® Homo-mixer.

The nail coating formulation was prepared from the following ingredients:

| Ingredients | Percent by Weight |
| --- | --- |
| Emulsion polymer of Example 2 | 92.39 |
| Color concentrate as prepared above | 4.55 |
| Dimethyl silicone | 0.01 |
| Thickener as prepared above | 3.00 |
| Benzophenones (mixed) | 0.05 |
| | 100.00 |

The emulsion polymer was placed in a mixing vessel and the second ingredient was slowly added with medium agitation by a Gifford-Wood ® Homo-mixer. The third and fourth ingredients were added sequentially with stirring and the fifth ingredient was then added with very slow stirring.

The unit formulation of the above nail coating formulation was determined. The unit formulation represents the percentages of all ingredients as they would appear in the final formulation. The unit formulation is shown in the following table.

| Class of Ingredient | Ingredients | Percent by Weight |
| --- | --- | --- |
| Emulsion polymer | Emulsion Polymer of Example 2 | 92.39 |
| Pigment/dye | Iron oxide, synthetic brown | 1.50 |
| Dispersing agent | Tamol ® 731 (25 percent) | 0.03 |
| Wetting agent | Triton ® CF 10 | 0.02 |
| Thickener | Natrosol ® 250 M | 0.06 |
| Coalescing agent | None | 0.00 |
| Preservative | Methyl paraben | 0.25 |
| Preservative | Potassium sorbate | 0.30 |
| Antifoam | Dimethyl silicone | 0.01 |
| Chelating agent | EDTA . Na4 | 0.02 |
| Buffer | None | 0.00 |
| UV absorber | Benzophenone (mixed) | 0.05 |
| Water | Distilled water | 5.37 |
| | | 100.00 |

EXAMPLE 27

The color concentrate for the nail coating formulation was prepared from the following ingredients:

| Ingredients | Percent by Weight |
| --- | --- |
| Carmine | 50.000 |
| 0.1 percent aqueous solution of tetrasodium pyrophosphate | 0.005 |
| Deionized water | 49.995 |
| | 100.000 |

The second and third ingredients were placed in an Osterizer ® blender and stirred. The first ingredient was added and slowly stirred with scraping of the sides of the blender until the formulation was thoroughly mixed.

A 2 percent methylcellulose in water preparation was prepared with the following ingredients:

| Ingredients | Percent by Weight |
| --- | --- |
| Methocel ®, Dow, 250 M (methylcellulose) | 2.00 |

| Ingredients | Percent by Weight |
| --- | --- |
| 37 percent aqueous solution of formaldehyde | 1.67 |
| Deionized water | 96.33 |
| | 100.00 |

The third ingredient was placed in a mixing vessel and the second ingredient was agitated with a Gifford-Wood ® Homo-mixer at room temperature. The first ingredient was added to the mixture and milled until uniform.

The nail coating formulation was then prepared in the following manner:

| Ingredients | Percent by Weight |
| --- | --- |
| Emulsion polymer of Example 12 | 77.9 |
| Color concentrate prepared above | 14.0 |
| 2 percent methylcellulose prepared as above | 6.0 |
| Dehydroacetic acid | 0.1 |
| Butylcellosolve™, Union Carbide, (ethyleneglycol monobutyl ether) | 2.0 |
| | 100.0 |

The second ingredient was added to the first ingredient in a mixing vessel with milling at high speed by a Gifford-Wood ® Homo-mixer to shear and disperse the mixture. Ingredient three was then added to the mixture and milled until the mixture was uniform. Ingredient four was then added to the mixture and milled. Ingredient five was finally added to the mixture and milled until the mixture was uniform to form the final nail coating formulation.

The unit formulation for the final product was determined and is given in the following table.

| Class of Ingredient | Ingredients | Percent by Weight |
| --- | --- | --- |
| Emulsion polymer | Emulsion polymer of Example 12 | 77.9 |
| Pigment/dye | Carmine | 7.00 |
| Dispersing agent | Tetrasodium pyrophosphate (0.01%) | 0.0007 |
| Wetting agent | None | 0.00 |
| Thickener | Methocel ® 250 M | 0.12 |
| Coalescing agent | Butylcellosolve™ | 2.00 |
| Preservative | 37 percent aqueous formaldehyde | 0.10 |
| Preservative | Dehydroacetic acid | 0.10 |
| Antifoam | None | 0.00 |
| Chelating agent | None | 0.00 |
| Buffer | Alkaline borate buffer pH 8.6 (5 ml.) | — |
| UV absorber | None | 0.00 |
| Water | Distilled water | 12.7793 |
| | | 100.00 |

EXAMPLE 28

The color concentrate for the nail coating formulation was prepared from the following ingredients:

| Ingredients | Percent by Weight |
| --- | --- |
| D&C Red No. 9 Barium Lake | 46.3 |

-continued

| Ingredients | Percent by Weight |
|---|---|
| Deionized water | 46.3 |
| Tergitol ®, Union Carbide, NP 27 (1:7 nonylphenol:-ethylene oxide condensate) | 4.2 |
| Alcolec ®, American Lechitin, HS-2 (sulfonated soya lechitin) | 3.2 |
| | 100.0 |

Ingredients three and four were mixed into ingredient two in an Osterizer ®. Using a high rate of speed, the first ingredient was dispersed into the mixture. The speed was reduced and the mixture was stirred until uniform.

A polyvinyl alcohol solution, 20 percent, was prepared in the following manner:

| Ingredients | Percent by Weight |
|---|---|
| Polyvinyl alcohol (Gelvatol$^{TM}$ 20-60, Monsanto) (Partially hydrolyzed) | 20.0 |
| Deionized water | 80.0 |
| | 100.0 |

On a magnetic stirrer hotplate using a high speed of stirring, the first ingredient was mixed quickly into the second ingredient and heated to 80° C. The mixture was stirred constantly until a highly viscous solution was obtained.

The nail coating formulation was prepared from the following ingredients:

| Ingredients | Percent by Weight |
|---|---|
| Emulsion polymer of Example 3 | 77.90 |
| Color concentrate prepared above | 10.80 |
| Polyvinyl alcohol solution prepared above | 5.00 |
| Diacetone alcohol (4-hydroxy-4-methyl-2-pentanone | 6.00 |
| Dowicil ®, Dow, 200 [1-(3-chloroallyl)-3,5,7-triaza-1-azoniaadamantane chloride] | 0.10 |
| Pluronic ®, BASF Wyandott, L-61 (1:10 polyoxyethylene:-polyoxypropylene condensate, MW about 1750) | 0.05 |
| Citric acid | 0.10 |
| Dioxybenzone | 0.05 |
| Water | 9.00 |
| | 100.00 |

The second ingredient was dispersed into the first ingredient in a mixing vessel using a Gifford-Wood ® Homo-mixer. The third ingredient was then added to the mixture and milled until uniform. The remaining ingredients were then added in the order given with thorough milling between additions.

The unit formulation for the resulting nail coating is as shown in the following table.

| Class of Ingredient | Ingredients | Percent by Weight |
|---|---|---|
| Emulsion polymer | Emulsion polymer of Example 3 | 77.90 |
| Pigment/dye | D&C Red No. 9 | |

-continued

| Class of Ingredient | Ingredients | Percent by Weight |
|---|---|---|
| | Barium Lake | 5.00 |
| Dispersing agent | Alcolec ® HS-2 | 0.45 |
| Wetting agent | Tergitol ® NP 27 | 0.35 |
| Thickener | Polyvinyl alcohol | 1.00 |
| Coalescing agent | Diacetone alcohol | 6.00 |
| Preservative | Dowicil ® 200 | 0.10 |
| Antifoam | Pluronic ® L-61 | 0.05 |
| Chelating agent | Citric acid | 0.10 |
| Buffer | None | 0.00 |
| UV absorber | Dioxybenzone | 0.05 |
| Water | Distilled water | 9.00 |
| | | 100.00 |

EXAMPLE 29

The following nail coating formulation was prepared from the following ingredients:

| Ingredients | Percent by Weight |
|---|---|
| Emulsion polymer of Example 10 | 97.4875 |
| D&C Red No. 22 | 0.50 |
| Methylcarbitol (diethyleneglycol monomethyl ether) | 2.00 |
| Phenylmecuric acetate | 0.01 |
| Antifoam$^{TM}$H-10 (silicone emulsion H-10, Dow Corning | 0.0025 |
| | 100.0000 |

Each ingredient was added in order and thoroughly mixed with a paddle mixer.

The unit formulation is shown in the following table.

| Class of Ingredient | Ingredients | Percent by Weight |
|---|---|---|
| Emulsion polymer | Emulsion polymer of Example 10 | 97.4875 |
| Pigment/dye | D&C Red No. 22 | 0.5000 |
| Dispersing agent | None | 0.0 |
| Wetting agent | None | 0.0 |
| Thickener | None | 0.0 |
| Coalescing agent | Methylcarbitol | 2.0000 |
| Preservative | Phenylmecuric acetate | 0.0100 |
| Antifoam | Antifoam$^{TM}$ H-10 | 0.0025 |
| Chelating agent | None | 0.0 |
| Buffer | None | 0.0 |
| UV absorber | None | 0.0 |
| Water | Distilled water | 0.0 |
| | | 100.0000 |

EXAMPLE 30

This nail coating preparation consisted of just the emulsion polymer used as a clear coating. The polymer used was the emulsion polymer prepared in Example 9.

EXAMPLE 31

The thickener for the coating formulation was prepared from the following ingredients:

| Ingredients | Percent by Weight |
|---|---|
| Polyvinyl alcohol (Gelvatol$^{TM}$20-60, Monsanto) (partially hydrolyzed) | 20.0 |
| Methyl paraben (methyl p-hydroxy- | 2.0 |

-continued

| Ingredients | Percent by Weight |
|---|---|
| benzoate) | |
| Deionized water | 78.0 |
| | 100.0 |

On a magnetic stirrer hot plate using a high speed of stirring, the second ingredient was mixed quickly into the third ingredient, heated to 80° C., and stirred until dissolved. The mixture was stirred at high speed and ingredient one quickly added. The mixture was stirred constantly until a highly viscous solution was obtained.

The nail coating formulation was prepared from the following ingredients:

| Ingredients | Percent by Weight |
|---|---|
| Emulsion polymer of Example 9 | 94.9975 |
| Thickener prepared above | 5.0000 |
| Antifoam$^{TM}$H-10 (silicone emulsion H-10, Dow Corning) | 0.0025 |
| | 100.0000 |

The third ingredient was dispersed into the first ingredient in a mixing vessel using a Gifford-Wood® Homo-mixer. The second ingredient was then added to the mixture and milled until uniform and smooth.

The unit formulation for the resulting nail coating is as shown in the following table.

| Class of Ingredient | Ingredients | Percent by Weight |
|---|---|---|
| Emulsion polymer | Emulsion polymer of Example 9 | 94.9975 |
| Pigment/dye | None | 0.0 |
| Dispersing agent | None | 0.0 |
| Wetting agent | None | 0.0 |
| Thickener | Polyvinyl alcohol | 1.0000 |
| Coalescing agent | None | 0.0 |
| Preservative | Methyl paraben | 0.1000 |
| Antifoam | Antifoam$^{TM}$H-10 | 0.0025 |
| Chelating agent | None | 0.0 |
| Buffer | None | 0.0 |
| UV absorber | None | 0.0 |
| Water | Distilled water | 3.9000 |
| | | 100.0000 |

EXAMPLE 32

Two weight percent of ethyleneglycol monobutyl ether as a coalescing agent was added to the nail coating of Example 31 with gentle stirring with a paddle mixer. The unit formulation was thereby modified slightly from Example 31.

What is claimed is:

1. A nail coating formulation which upon drying forms a film which will adhere to keratin of the nail and has a moisture vapor transmission from about 0.1 to about 1.6 mg./cm.$^2$/hr., said formulation comprising an aqueous emulsion polymer having a solids content from about 30 to about 55 percent, the polymer having a T$_g$ within the range of about $-10°$ C. to about 50° C. when measured by differential thermal analysis and being prepared by an aqueous emulsion polymerization of two or more of the following monomers, at least one of which is of formula I or formula II;

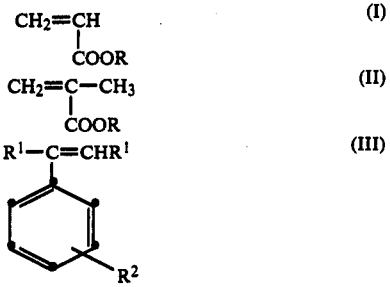

wherein R is C$_1$-C$_{20}$ alkyl, phenyl, benzyl, hydroxy-(C$_1$-C$_4$)-alkyl, C$_1$-C$_4$ alkoxy-(C$_1$-C$_4$)alkyl, cyclopentyl, cyclohexyl, furyl, C$_1$-C$_4$ alkylfuryl, tetrahydrofuryl, or C$_1$-C$_4$ alkyltetrahydrofuryl; R$^1$ is hydrogen or methyl; and R$^2$ is hydrogen or C$_1$-C$_3$ alkyl, subject to the limitation that when R in one of the monomers is C$_1$-C$_4$ alkoxy-(C$_1$-C$_4$)alkyl, then R in the other monomer is a group other than C$_1$-C$_4$ alkoxy-(C$_1$-C$_4$)alkyl or hydroxy-(C$_1$-C$_4$)alkyl.

2. The formulation of claim 1 wherein R is C$_1$-C$_8$ alkyl and R$^1$ is hydrogen.

3. The formulation of claim 1 wherein the polymer has a T$_g$ of from about 10° to about 30° C.

4. The formulation of claim 1 wherein the emulsion polymer has a solids content from about 35 to about 45 percent.

5. The formulation of claim 1 wherein the number of monomers used to prepare the emulsion polymer is from 2 to 4.

6. The formulation of claim 1 wherein an additional monomer is employed in the preparation of the polymer, in an amount not exceeding 10 percent by weight.

7. The formulation of claim 6 wherein the additional monomer is a cross linking agent.

8. The formulation of claim 2 wherein one of the monomers is 2-ethylhexyl acrylate.

9. The formulation of claim 2 wherein one of the monomers is ethyl acrylate.

10. The formulation of claim 2 wherein one of the monomers is butyl acrylate.

11. The formulation of claim 2 wherein one of the monomers is methyl methacrylate.

12. The formulation of claim 2 wherein one of the monomers is ethyl methacrylate.

13. The formulation of claim 1 wherein one of the monomers is styrene.

14. The formulation of claim 1 wherein one of the monomers is 4-vinyltoluene.

15. The formulation of claim 6 wherein methacrylic acid is employed as an additional monomer.

16. The formulation of claim 1 wherein a pigment or dye is included.

17. The formulation of claim 1 wherein a dispersing agent is included.

18. The formulation of claim 1 wherein a wetting agent is included.

19. The formulation of claim 1 wherein a thickener is included.

20. The formulation of claim 1 wherein a coalescing agent is included.

21. The formulation of claim 1 wherein a preservative is included.

22. The formulation of claim 1 wherein an antifoam agent is included.

23. The formulation of claim 1 wherein a chelating agent is included.

24. The formulation of claim 1 wherein a UV absorber is included.

* * * * *